US00PP37814P3

(12) United States Plant Patent
Skotak, Jr.

(10) Patent No.: US PP37,814 P3
(45) Date of Patent: Oct. 20, 2026

(54) ***AECHMEA* PLANT NAMED 'A4005'**

(50) Latin Name: ***Aechmea* hybrid**
Varietal Denomination: A4005

(71) Applicant: Chester Skotak, Jr., Alajuela (CR)

(72) Inventor: Chester Skotak, Jr., Alajuela (CR)

( * ) Notice: Subject to any disclaimer, the term of this patent is extended or adjusted under 35 U.S.C. 154(b) by 0 days.

(21) Appl. No.: 19/393,355

(22) Filed: Nov. 18, 2025

(65) Prior Publication Data

US 2026/0157247 P1 Jun. 4, 2026

(30) Foreign Application Priority Data

Nov. 29, 2024 (QZ) ..... PBR 2024/2859

(51) Int. Cl.
*A01H 6/22* (2018.01)
*A01H 5/02* (2018.01)
*A01H 5/12* (2018.01)

(52) U.S. Cl.
USPC ..... Plt./370
CPC ..... *A01H 6/22* (2018.05); *A01H 5/02* (2013.01); *A01H 5/12* (2013.01)

(58) Field of Classification Search
USPC ..... Plt./263.1, 370
See application file for complete search history.

(56) References Cited

U.S. PATENT DOCUMENTS

PP35,740 P2 * 4/2024 Gomez Bullis ..... Plt./370

* cited by examiner

*Primary Examiner* — Karen M Redden
(74) *Attorney, Agent, or Firm* — James R. Holm; Plant Novelty Rights, LLC

(57) ABSTRACT

A new and distinct *Aechmea* plant named 'A4005' particularly distinguished by a compact plant habit with a tightly formed rosette; inflorescence with shorter and denser spikes; a unique blue inflorescence coloration, including bluish bracts and violet-blue flowers; moderate vigor and a uniform growth habit; and an excellent presentation and stability in commercial potted plant production.

3 Drawing Sheets

Figure 1:
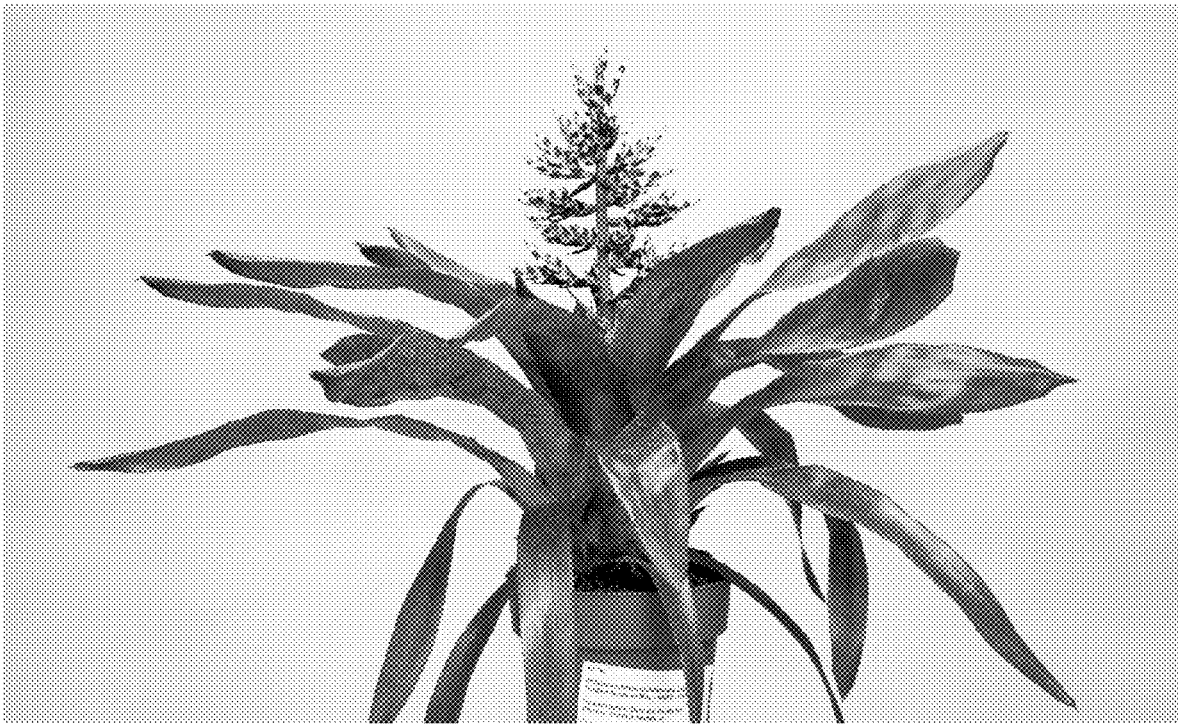

Genus and species: *Aechmea* hybrid.
Variety denomination: 'A4005'.

STATEMENT REGARDING PRIOR DISCLOSURES BY THE INVENTOR

This application claims priority to CPVO application no. 2024/2859 filed on Nov. 29, 2024, which is herein incorporated by reference. The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period prior to the filing date.

BACKGROUND OF THE NEW PLANT

The present invention comprises a new and distinct variety of *Aechmea* plant, botanically known as *Aechmea* hybrid, and hereinafter referred to by the variety name 'A4005'.

*Aechmea* comprises a genus of more than 168 species of evergreen perennials suitable for cultivation in the home or in the greenhouse. *Aechmea* may be terrestrial or epiphytic. For the most part, the species vary in diameter from 12 to 18 inches to 3 or 4 feet and have rosettes of spiny-edged leaves.

Flowers and bracts of *Aechmea* frequently have brilliant colors and may last for several months. The range of colors for *Aechmea* is generally from the yellow through orange but may also include pink, orange, red and red-purple. Tubular, three-petalled flowers may also appear but are usually short-lived.

*Aechmea* may be grown as pot plants for greenhouse or home use. Typically, the plants are shaded from direct sunlight; and the central, vaselike part of the leaf rosette is normally filled with water.

*Aechmea* is native to tropical America. Leaves of *Aechmea* are usually formed from basal rosettes which are entire and in several vertical ranks. *Aechmea* has terminal spikes or panicles which are often bracted with petals united in a tube longer than the calyx.

Asexual propagation of *Aechmea* is frequently done through meristematic tissue culture. Propagation can also be from offshoots which can be detached from the mother plant and grown in an appropriate soil or bark mixture. Methods for cultivating and crossing of *Aechmea* are well known.

The new *Aechmea* variety 'A4005' is the product of a controlled cross pollination conducted by the inventor in May 2015. The objective of the breeding program was to produce a compact hybrid *Aechmea* with a denser, shorter inflorescence and distinctive blue coloration. Both the female and male parents are unpatented and unnamed breeding selections of *Aechmea hybrida* which was derived from *Aechmea* hybrida 'Blue Tango' (*Aechmea dichlamydea* var. *trinitensis* x *Aechmea fendleri*) (expired U.S. Plant Pat. No. 11,743). 'A4005' was selected by the inventor in 2021 in Alajuela, Costa Rica as a single flowering plant from within the progeny of the stated cross.

The new *Aechmea* cultivar 'A4005' was first reproduced asexually by meristematic tissue culture in January 2020 at a commercial laboratory in Evergem, Belgium. Asexual propagation by meristematic tissue culture of the new variety has shown that the unique features of the new variety are stable and reproduced true-to-type to date through 7 successive generations.

SUMMARY OF THE INVENTION

The new *Aechmea* cultivar 'A4005' has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Aechmea* cultivar. The combination of these characteristics distinguishes 'A4005' as a new and distinct variety of *Aechmea*.

1. *Aechmea* 'A4005' exhibits a compact plant habit with a tightly formed rosette.
2. *Aechmea* 'A4005' exhibits compact inflorescence with shorter and denser spikes.
3. *Aechmea* 'A4005' exhibits a unique blue inflorescence coloration, including bluish bracts and violet-blue flowers.
4. *Aechmea* 'A4005' exhibits moderate vigor and a uniform growth habit.
5. *Aechmea* 'A4005' exhibits an excellent presentation and stability in commercial potted plant production.

DESCRIPTION OF THE PHOTOGRAPHS

This new *Aechmea* cultivar is illustrated by the accompanying-colored photographs which show the overall appearance and distinct characteristics of the plant. The colors shown are as true as can be reasonably obtained by conventional photographic procedures. The photographs are of 24 to 26-month-old plants grown in 14-centimeter circular containers in a conventional glass greenhouse in Evergem, Belgium. Colors in the photographs may differ slightly from the color values cited in the botanical description which accurately describes the colors of the new variety.

FIG. 1. shows the overall plant form, foliage, and inflorescence of 'A4005'.

Figure 2:
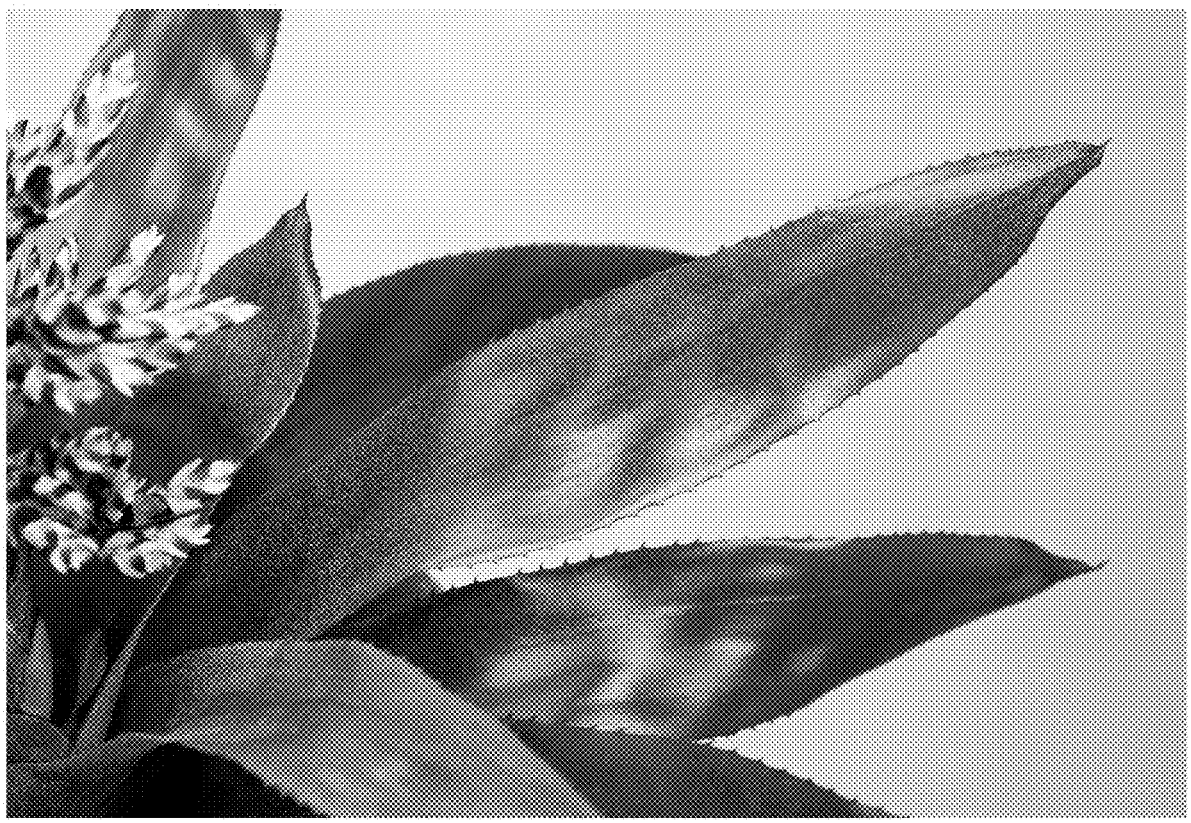

FIG. 2. shows a close-up of typical foliage of 'A4005'.

Figure 3:
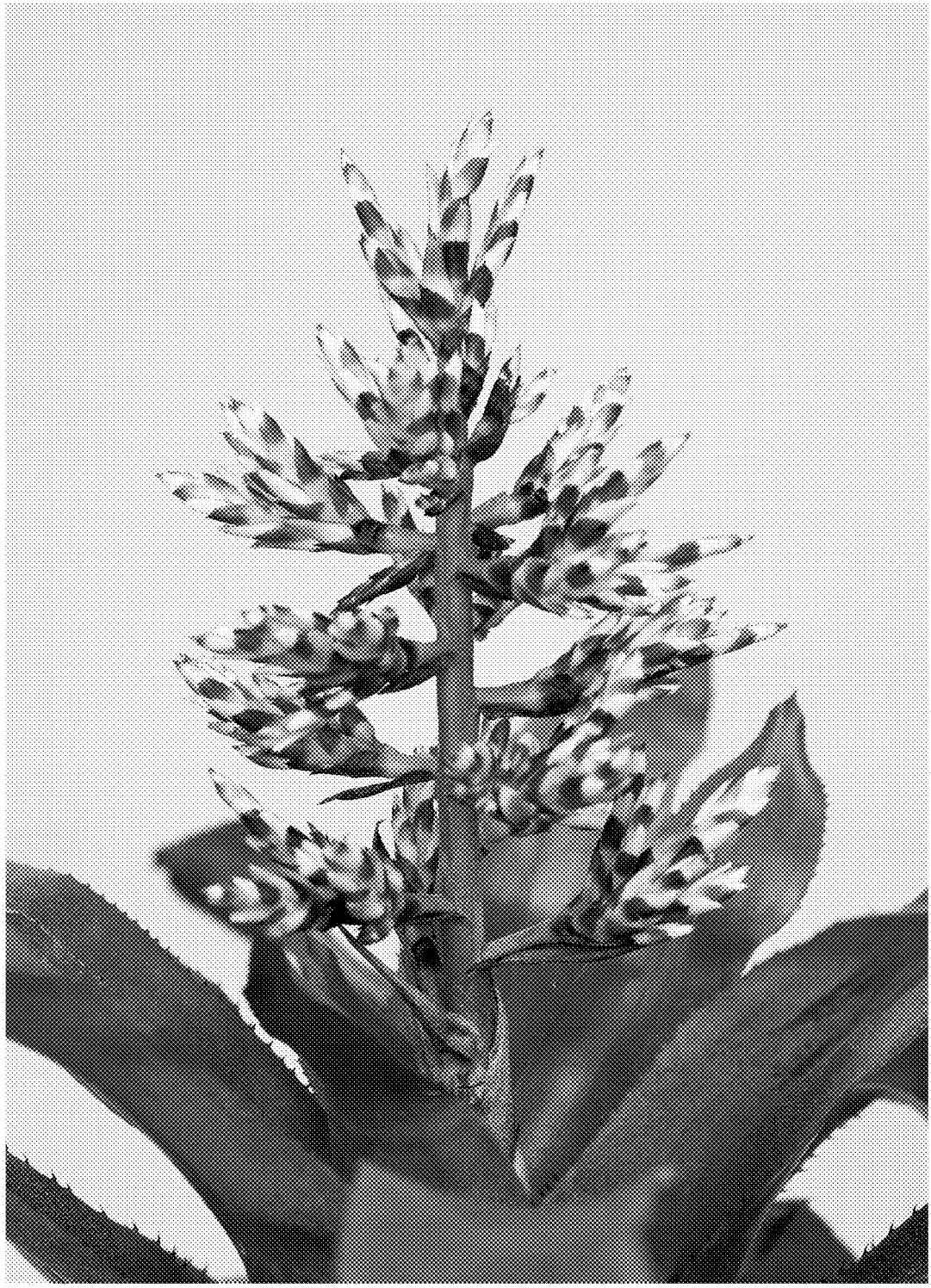

FIG. 3. shows a close-up of typical inflorescence of 'A4005'.

DESCRIPTION OF THE NEW VARIETY

In the following description, color references are made to The Royal Horticultural Society Colour Chart, Sixth Edition, except where general color terms of ordinary dictionary significance are used.

The following observations and measurements describe plants grown in a commercial greenhouse located in Evergem, Belgium. Plants were grown under maximum light levels of approximately 12,000 lux. Detailed descriptions were taken in November 2025 from 24 to 26-month-old plants grown in 14-centimeter circular containers. Measurements and numerical values represent averages of typical plant types.

DETAILED BOTANICAL DESCRIPTION

Classification:

*Family*.—Bromeliaceae.

*Botanical*.—*Aechmea* hybrid.

*Denomination*.—'A4005'.

General description:

*Plant type*.—Tropical perennial suitable as an indoor potted plant.

*Growth habit*.—Compact, basal rosette; inflorescence grows from the center of the basal rosette.

*Overall plant shape*.—Flattened to flattened globular with inflorescence carried slightly above the foliar plane.

*Height from soil level to top of foliar plane*.—Average 28.8 cm.

*Height from soil level to top of floral plane*.—Average 33.9 cm.

*Plant diameter or area of spread*.—Average 61.3 cm.

*Growth rate*.—Moderate.

*Plant vigor*.—Moderate.

*Branching habit*.—No lateral branching; leaves in a basal rosette, inflorescence grows from the center of the basal rosette.

*Basal branching*.—Occasionally secondary rosettes will grow from the base.

*Propagation type*.—Meristematic tissue culture.

Root description:

*General*.—Slightly fleshy and slightly fibrous.

*Length*.—7.3 cm.

*Diameter*.—0.1 cm.

*Color*.—165B (greyed-orange).

Foliage description:

*Arrangement*.—Rosulate.

*Division*.—Simple.

*Quantity of leaves per rosette*.—Average 30.

*Lamina*.—Shape: Oblong. Length: Average 35.0 cm. Width: Average 5.3 cm. Aspect: Moderately concave, slightly twisted axially and curled downward; leaf tips near horizontal. Apex shape: Acute with a sharp, abruptly acute tip. Base: Sheathing. Sheath length: Average 7.5 cm. Sheath width Average 7.4 cm. Sheath color: 146C and 146D (yellow-green). Margin: Dentate; teeth are sharp, pointed towards the leaf apex, and measure an average of 0.2 cm in length and colored 200A (brown). Undulation: Slightly coarsely undulate. Lobes: Unlobed. Texture (both upper and lower surfaces): Smooth, slightly covered with a thin waxy layer consisting of very small waxy dots having an average diameter of approximately 0.1 mm and colored N155A (white). Rugosity (both upper and lower surfaces): Non-rugose. Pubescence (both upper and lower surfaces): Not present. Luster: Upper surface: Glossy. Lower surface: Moderately glossy. Color: Juvenile foliage: Upper surface: 143A (green). Lower surface: A blend of 146A and 146B (yellow-green) and tipped darker 147A (yellow-green). Mature foliage: Upper surface: Slightly darker than a blend of NN137A and 147A (green to yellow-green) and slightly covered with a thin waxy layer consisting of small waxy dots having an average diameter of approximately 0.1 mm and colored N155A (white). Lower surface: NN137B (green) and covered with a thin waxy layer consisting of very small waxy dots having an average diameter of approximately 0.1 mm and colored N155A (white). Venation: Pattern: Parallel. Color (mature foliage): Upper surface: Upper surface venation is colored the same as the upper surface of the lamina. Lower surface: Lower surface venation is colored the same as the lower surface of the lamina.

Inflorescence description:

*Arrangement*.—Terminal panicle.

*Type and form*.—Panicle, consisting of a main panicle and an average of 13 secondary panicles, each consisting of an average of 26 individual flowers.

*Height*.—Average 18.0 cm.

*Diameter*.—Average 12.8 cm.

*Quantity of flowers and flower buds per inflorescence*.—Average 350.

*Natural flowering season*.—Continuously.

*Time to flower or response time*.—6 months.

*Flower bud*.—Length: Average 1.4 cm. Diameter: Flattened, average diameter at widest point, 0.3 cm, and average diameter at narrowest point, 0.25 cm. Shape: Oblong. Texture: Smooth and glabrous. Luster: Slightly glossy. Color: 155B (white) and 157C and 157D (green-white), fading to 94B (violet-blue) towards the top. Flower bud bract (positioned at the base of the flower bud): Shape: Broad ovate. Apex: Apiculate. Base: Cuneate. Margin: Entire. Length: 0.7 cm. Diameter: 0.4 cm. Color: A blend of N89A and N92B (violet-blue), fading to 73B and 73C (red-purple) towards the base.

*Flower*.—Type and form: Single, rotate. Aspect: Outwardly to upright. Habit: Freely. Fragrance: Not fragrant. Shape: Rotate, petals not opening but remaining in oblanceolate shape. Vertical height: Average 0.4 cm. Horizontal diameter: Average 0.4 cm. Length (depth): Average 1.6 cm. Tube texture: Smooth and glabrous. Longevity: Average 4 weeks. Persistence: Persistent.

*Petals*.—Arrangement: Rotate. Quantity per flower: Average 3. Number of petal whorls: Average 1. Petal fusion: Not fused. Length: Average 0.5 cm. Width: Average 0.15 cm. Shape: Ovate, concave. Tip: Acute. Base: Cuneate. Margin: Entire. Margin undulation: Not undulated. Texture (both upper and lower surfaces): Smooth and glabrous. Rugosity (both upper and lower surfaces: Non-rugose. Luster (both upper and lower surfaces): Moderately glossy. Color: When opening: Upper surface: 90C (violet-blue) fading to 157D (green-white) towards the base. Lower surface: A blend of 90B and 90C (violet-blue) fading to 157D (green-white) towards the base. When fully opened: Upper surface: 90C (violet-blue) fading to 155C (white) towards the base. Lower surface: A blend of 90B and 90C (violet-blue) fading to 155C (white) towards the base. When fading (both upper and lower surfaces): Non-fading. Venation: Inconspicuous. Petaloids: Not present.

*Calyx*.—Shape: Rotate. Length: Average 1.4 cm. Diameter: 0.4 cm.

*Sepals*.—Arrangement: Rotate. Quantity per flower: Average 3. Quantity of sepal whorls: 1. Length: Average 1.3 cm. Width: Average 0.5 cm. Sepal fusion: Not fused. Shape: Lanceolate, concave. Apex or tip: Abruptly acute. Base: Cuneate. Margin: Entire. Texture (both upper and lower surfaces): Glabrous and smooth. Luster (both upper and lower surfaces): Slightly glossy. Color when opening and fully opened: Upper surface: Transparent NN155B (white). Lower surface: Transparent NN155B (white) with a close to 90C (violet-blue) abruptly acute tip, however difficult to discern due to its small size. Sepal spurs: Not present.

*Peduncle*.—Terminal length: Average 31.1 cm. Terminal diameter: Average 0.8 cm. Angle: Vertical. Strength: Strong. Texture: Smooth, glabrous; lower portion (below panicle) is sparsely to moderately covered with short pubescence, rough to the touch, and colored 199C (grey-brown). Luster: Matte. Color: 180B and 180C (greyed-red); lower portion (below panicle) fades to a lighter 179B and 179C (greyed-red) with secondary peduncles colored 52A (red).

*Pedicels*.—Not Present, individual flowers sessile.

*Bracts* (*main peduncle*).—General description: An average of 9 bracts present on the main peduncle. Shape: Lanceolate. Length: Average 7.7 cm. Width: Average 4.8 cm. Luster (both sides): Matte. Margin: Entire. Apex: Narrow apiculate. Base: Broad cuneate. Color (both upper and lower surfaces): 145C (yellow-green), fading to 155C (white) towards the base; when mature, both surfaces fading to 200B (brown) when mature with N199C (grey-brown) towards the base.

*Bracts* (*secondary panicles*).—General description: A single fertile bract is present at the base of each secondary panicle. Shape: Narrow ovate to lanceolate. Length: Average 2.2 cm. Width: Average 0.7 cm. Luster (both sides): Matte. Margin: Entire. Apex: Narrow apiculate. Base: Broad cuneate. Color: Upper surface: 79B (purple). Lower surface: 79A (purple), fading lighter to N79A (purple) towards the base.

*Bracts* (*flowers*).—General description: A single bract present below each individual flower. Shape: Ovate. Apex: Apiculate. Base: Cuneate. Margin: Entire. Length: Average 0.7 cm. Width: 0.4 cm. Color: A blend of N89A and N92B (violet-blue), fading to 73B and 73C (red-purple) towards the base.

*Reproductive organs*.—Quantity of stamens per flower: 3. Filament: Length: Average 0.1 cm. Color: 155A (white). Anther: Shape: Dorsifixed, narrow elliptic. Length: Average 0.3 cm. Width: Average 0.1 cm. Color: 155C (white). Pollen amount: None observed. Pistil: Quantity: 1. Length: Average 0.5 cm. Stigma: Shape: Cleft; three-parted, stigmas fringed. Length: Average 0.1 cm. Diameter: Average 0.1 cm. Color: 155C (white). Style: Length: Average 0.4 cm. Color: 155C (white). Ovary color: 145C (yellow-green).

Fruit and seed set: None observed to date.

Temperature tolerances: USDA Zones 10 to 13; at least tolerant of temperatures to 40 degrees Celsius.

Rain tolerance: High.

Wind tolerance: High.

Disease and pest tolerance: No claims are made to any superior disease or insect resistance or tolerance.

COMPARISON WITH THE PARENT PLANTS

The new *Aechmea* cultivar 'A4005' can be distinguished from its female or seed parent in the following characteristics described in Table 1 below.

TABLE 1

| Characteristic | 'A4005' | Female parent |
|---|---|---|
| Overall plant size | Compact, flattened rosette | Medium, open rosette |
| Leaf margin | Finely serrulate | Finely serrulate |
| Leaf color | Slightly darker green | Medium green |
| Inflorescence length | Shorter, compact | Longer, elongated |
| Inflorescence color | Bluish-red rachis, blue-violet flowers | Red rachis, purple flowers |
| Flower density | Densely packed | Moderately spaced |
| Flower color | Deep violet blue | Violet-purple |

The new *Aechmea* cultivar 'A4005' can be distinguished from its male or pollen parent in the following characteristics described in Table 2 below.

TABLE 2

| Characteristic | 'A4005' | Male Parent |
|---|---|---|
| Rosette form | More compact | More spreading |
| Leaf length | Shorter | Longer |

TABLE 2-continued

| Characteristic | 'A4005' | Male Parent |
|---|---|---|
| Inflorescence length | Shorter and compact | Longer and looser |
| Bract color | Bluish-red | Red to reddish-purple |
| Flower color | Blue-violet | Violet-purple |
| Flower arrangement | Tightly packed | Loosely arranged |
| Overall plant habit | Compact, upright | Medium, arching |

COMPARISON WITH RELATED KNOWN VARIETY

The new *Aechmea* cultivar 'A4005' can be distinguished from the related known variety of *Aechmea* 'Blue Tango' in the following characteristics described in Table 3 below.

TABLE 3

| Characteristic | 'A4005' | 'Blue Tango' |
|---|---|---|
| Plant Compactness | More compact | Less compact |
| Length of inflorescence | Shorter | Longer |
| Overall shape of inflorescence | More compact, tight branches | Less compact, loose branches |
| Inflorescence color | Bluish-red rachis, blue-violet flowers | Reddish-purple rachis, violet flowers |

What is claimed is:

1. A new and distinct cultivar of *Aechmea* plant named 'A4005', substantially as illustrated and described herein.

* * * * *